United States Patent [19]

Zanakis et al.

[11] Patent Number: 4,951,674
[45] Date of Patent: Aug. 28, 1990

[54] BIOMAGNETIC ANALYTICAL SYSTEM USING FIBER-OPTIC MAGNETIC SENSORS

[76] Inventors: Michael F. Zanakis, 60 Martin Rd., Livingston, N.J. 07039; Philip A. Femano, 69 Alexander Ave., Nutley, N.J. 07110

[21] Appl. No.: 325,942
[22] Filed: Mar. 20, 1989
[51] Int. Cl.$^5$ .............................................. A61B 5/04
[52] U.S. Cl. ................................ 128/653 R; 128/731; 324/244.1
[58] Field of Search ............. 324/244 OP; 128/653 R, 128/639, 630, 731, 732

[56] References Cited

U.S. PATENT DOCUMENTS 4,591,787 5/1986 Hoening .............................. 324/260
4,771,239 9/1988 Hoenig .............................. 128/653 R

OTHER PUBLICATIONS

"Introduction to Magnetoencephalography—A New Window on the Brain", Biomagnetic Technologies, Inc., San Diego, Calif., undated.
Kersey et al., Journal of Lightwave Technology, vol. LT-3, No. 4, Aug. 1985, pp. 836–840.
Enokiharae et al., Journal of Lightwave Technology, vol. LT-5, No. 11, Nov. 1987, pp. 1584–1590.
Mermelstein, Journal of Lightwave Technology, vol. LT-4, No. 9, Sep. 1986, pp. 1376–1380.
Koo et al., Journal of Lightwave Technology, vol. LT-5, No. 12, Dec. 1987, pp. 1680–1684.
Yariv et al., Optics Letters, vol. 5, No. 3, Mar. 1980, pp. 87–89.
Koo et al., Optics Letters, vol. 7, No. 7, Jul. 1982, pp. 334–336.
Koo et al., J. Lightwave Tech., vol. LT-1, No. 3, Sep. 1983, pp. 524–525.

Primary Examiner—Lee S. Cohen
Assistant Examiner—John C. Hanley
Attorney, Agent, or Firm—Michael Ebert

[57] ABSTRACT

A biomagnetic analytical system for sensing and indicating minute magnetic fields emanating from the brain or from any other tissue region of interest in a subject under study. The system includes a magnetic pick-up device constituted by an array of fiber-optic magnetic sensors mounted at positions distributed throughout the inner confines of a magnetic shield configured to conform generally to the head of the subject or whatever other body region is of interest. Each sensor yields a light beam whose phase or other parameter is modulated in accordance with the magnetic field emanating from the related site in the region. The modulated beam from each sensor is compared in an interferometer with a reference light beam to yield an output signal that is a function of the magnetic field being emitted at the related site. The output signals from the interferometer are processed to provide a display or recording exhibiting the pattern or map of magnetic fields resulting from emanations at the multitude of sites encompassed by the region.

8 Claims, 2 Drawing Sheets

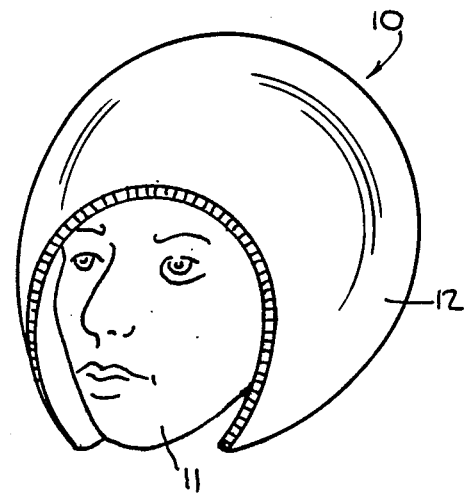
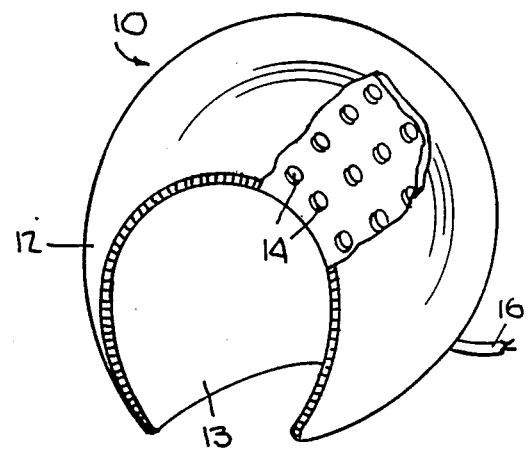
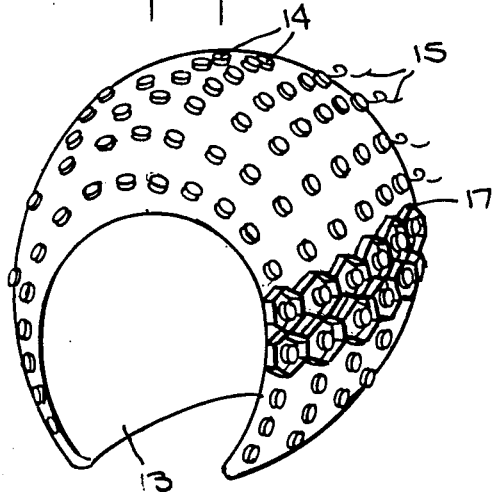
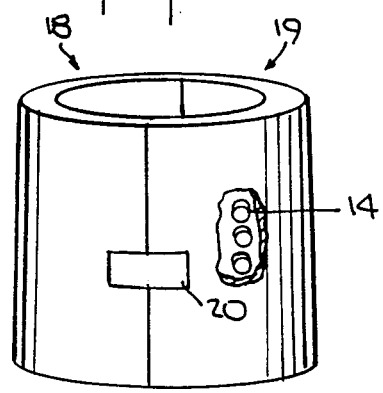
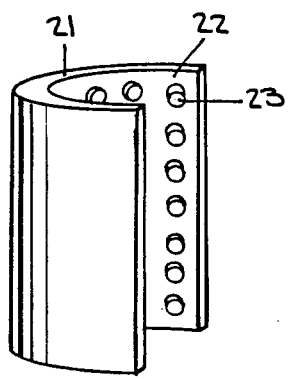
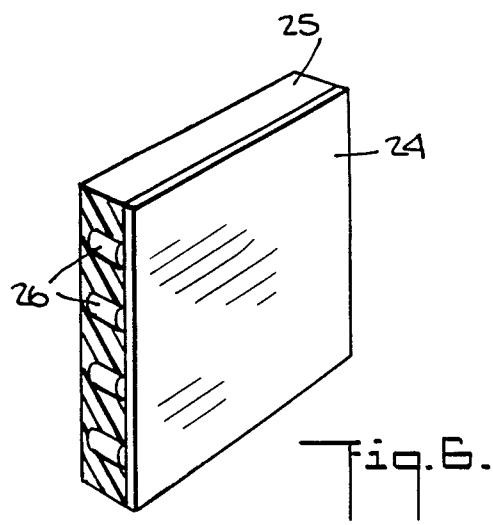

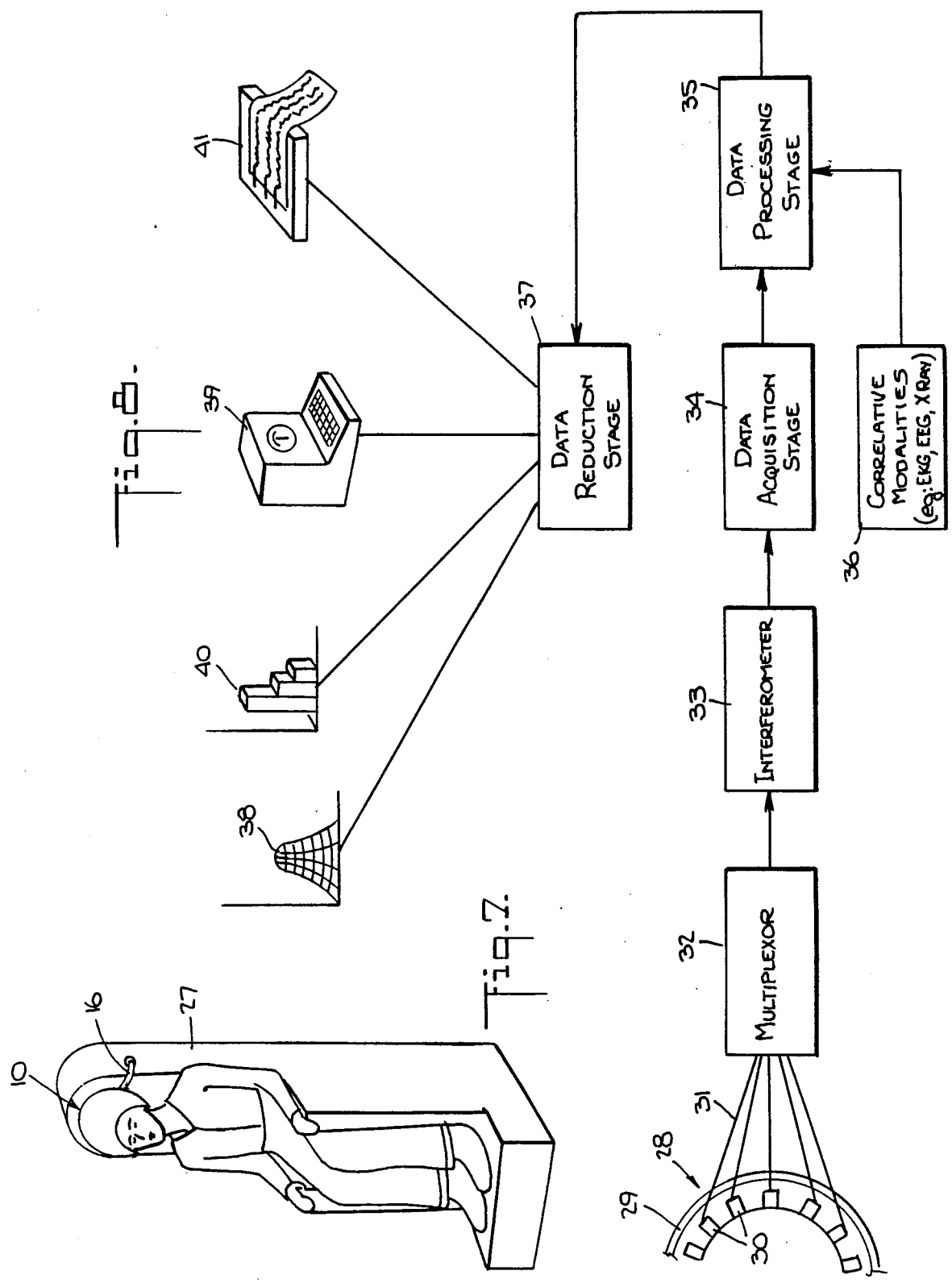

BIOMAGNETIC ANALYTICAL SYSTEM USING FIBER-OPTIC MAGNETIC SENSORS

BACKGROUND OF INVENTION

1. Field of Invention

This invention relates generally to biomagnetic analytic systems for sensing and indicating minute magnetic fields emanating from the brain and other tissue regions of the human body, and more particularly to a system using fiber-optic magnetic sensor pick-up devices for this purpose.

2. Status of Prior Art

Biomagnetic fields arise from three principal sources, the first being electric currents produced by the movement of ions. The second source is remanent magnetic movement of contaminants, and the third is paramagnetic or diamagnetic constituents of the body.

The first source is of primary significance in human brain activity in which the currents creating the magnetic fields result from signals generated by neurons as they communicate with each other and with sensory organs of the body. The intensity of extracranial magnetic field produced by such currents is extremely minute, having a strength no more than about a billionth of the magnetic field at the earth's surface. It is usually measured in terms of tesla (T) or gauss (G), one T being equal to $10^4$ G.

The magnetic field arising from spontaneous brain activity (alpha waves) is about one picotesla ($IpT = 10^{-12}T$), whereas the magnetic field at the earth's surface is about $6 \times 10^{-5}T$. The magnetic field emanating from the brain has a strength much below that emitted by the heart. Hence monitoring of brain magnetic activity presents formidable difficulties.

A major concern of the present invention is magnetoencephalography (also commonly referred to as MEG). This is the recording of magnetic fields emanating from the brain resulting from neuronal electric currents, as distinguished from an electroencephalogram (EEG) in which electric potentials originating in the brain are recorded. With an EEG measurement, it is difficult to extract the three-dimensional distribution of electrically active brain sites from potentials developed at the scalp. While this difficulty can be overcome by inserting electrodes through apertures bored in the skull, this invasive technique is not feasible in the study of normal brain functions or to diagnose functional brain disorders or brain dysfunctions. Thus ionic currents associated with the production of electrically measurable epileptic seizures generate detectable extracranial magnetic fields, and these can be detected externally without invading the skull.

Non-invasive MEG procedures are currently used in epilepsy research to detect the magnetic field distribution over the surface of the head of a patient with a view to localizing the seizure foci and spread patterns. This analysis serves as a guide to surgical intervention for the control of intractable seizures. (See: "Magnetoencephalography and Epilepsy Research"—Rose et al.; Science—16 Oct. 1987—Volume 238, pp. 329-335.)

MEG procedures have been considered as a means to determine the origin of Parkinson's tremor, to differentiate at the earliest possible stage Alzheimer's disease from other dementias, and to localize the responsible cortical lesions in visual defects of neurological origin. MEG procedures are also of value in classifying active drugs in respect to their effects on specific brain structures, and to in this way predict their pharmaceutical efficacy. And with MEG, one can gain a better understanding of the recovery process in head trauma and strokes by observing the restoration of neurological functions at the affected site.

But while MEG holds great promise in the above-noted clinical and pharmaceutical applications, practical considerations, mainly centered on limitations inherent in magnetic sensors presently available for this purpose, have to a large degree inhibited these applications.

The characteristics of biomagnetic activity that are measurable are the strength of the field, the frequency domain and the nature of the field pattern outside of the body. In magnetoencephalography, measurement of all three of these components are important. Ideally, simultaneous measurement of three orthogonal components of the magnetic field provides a complete description of the field as a function of space and time. Coincident measurement of the magnetic field along the surface of the skull can provide a magnetic field map of the cortical and subcortical magnetic activity. With spontaneous activity, the brain emits magnetic fields of about $10^{-8}$ to $10^{-9}$ Gauss, compared with approximately $10^{-6}$ Gauss emitted by the heart. Thus, monitoring of the brain's magnetic activity places heavy demand upon the required hardware.

In brain activity, the current dipole or source is generated by the current flow associated within a neuron or group of neurons. Volume current is analogous to the extracellular component of the current source. In MEG, the net magnetic field measured depends on the magnetic field generated by the current dipole itself. The contribution from volume conduction is small in which approximations to spherical symmetry are made. However, there are tangential magnetic components originating from secondary sources representing perturbations of the pattern by the volume current at boundaries between regions of different conductivity. Contributions from these secondary sources to the tangential component of the field become relatively more pronounced with distance from the current dipole. But there is no interference from these secondary sources when measurement is confined to the magnetic fields perpendicular to the skull.

In biomagnetic analysis, three types of magnetic sensors are known to have adequate sensitivy and discrimination against ambient noise for this purpose. (See: "Magnetoencephalography"—Sato et al.—Journal of Clinical Neurophysiology—Vol. 2, No. 2—1985.) The first is the induction coil. But because of Nyquist noise associated with the resistance of the windings and its loss of sensitivity at frequencies below a few Herz, the induction coil is rarely used in MEG studies.

The second is the Fluxgate magnetometer; and while this has been used in geophysical studies, it has certain drawbacks when used in MEG applications. It is for this reason that the third type, the SQUID system, is presently used almost exclusively in MEG applications.

A SQUID (Superconducting QUantum Interference Device) comprises a superconducting loop incorporating a "weak link" highly sensitive to the magnetic field encompassed within the area of the loop. While the loop itself can act as a magnetic field sensor, use is made of a detection coil tightly coupled to the superconducting loop, the coil acting as a flux transformer. Both the coil and the loop are immersed in a bath of liquid helium contained within a dewar.

With the advent of so-called high-temperature superconductors operating at liquid nitrogen temperatures, a SQUID magnetometer has been developed using such superconductors. (See: "The Impact of High Temperature Superconductivity on SQUID Magnetometers"—Clarke et al.—Science—Vol. 242—14 Oct. 1988.)

In the booklet published by Biomagnetic Technologies, Inc., of San Diego, Calif., entitled "Introduction to Magnetoencephalography—A New Window on The Brain," there is disclosed a SQUID-type sensor for MEG studies. This SQUID is especially suited to measure magnetic fields in the frequency range from DC to 20 kHz, the magnetic field being converted into a signal that is amplified, filtered and displayed for subsequent analysis.

Because the brain's field falls off sharply with distance from the head, the dewar for the cryogenic liquid, which is inherently bulky, is provided with a tail section of reduced diameter to house the pick-up coil and to minimize the distance of the coil from the head of the patient being studied, thereby maximizing the detected field.

As pointed out in the above-identified booklet, in order to produce a contour map of the brain, the magnetic field must be measured simultaneously at a number of points outside the head. While it is possible with SQUIDS to sample the magnetic field emanating from the brain at one to seven points separated laterally from each other by several centimeters, a complete mapping of the field pattern at a given instant requires forty or more pick-up points. It is proposed, therefore, in the booklet to move SQUID sensors from one point to another to accumulate the required field data. But a measurement taken at a point X will not reveal magnetic brain activity taking place concurrently at a point Y if one has to physically shift the sensor from point X to point Y.

The booklet notes that the ultimate goal of MEG measurement is to simultaneously observe all areas of the brain to produce real-time activity maps responding instantaneously to changes as they occur. However, the booklet concedes that this goal has not yet been realized with SQUID sensors.

The present invention attains this goal by means of fiber-optic magnetometers (FOM). In a FOM sensor, a magnetostrictive alloy is interfaced with an optical fiber to produce a magnetometer whose principle of operation is based on the transference of strain from the magnetostrictive material to the core of the optical fiber via mechanical bonding. This results in modulation of the phase or other parameters of the light propagated in the fiber which is subsequently detected by a fiber-optic interferometer. Integrated fiber-optic magnetometers in which all components are fabricated on or around the optical fibers are now known.

FOM sensors of the type currently available are far less expensive to manufacture and maintain than SQUID sensors; they are considerably more compact, and they operate at room temperature. Their sensitivity to weak magnetic fields, which can be greater than that of a SQUID, renders them suitable for MEG and other applications.

The following publications disclose various forms of FOM sensors:

1. "Single-Mode Fiber-Optic Magnetometer with DC Bias Field Stabilization"—Kersey et al.—Journal of Lightwave Technology—Vol. LT-3, No. 4—August 1985.

2. "Fiber-Optic Polarimetric DC Magnetometer Utilizing a Composite Metallic Glass Resonator"—Mermelstein—Journal of Lightwave Technology, Vol. LT-4, No. 9—September 1986.

3. "Optical Fiber Sensors Using The Method of Polarization-Rotated Reflection"—Enokihara et al.—Journal of Lightwave Technology—Vol. LT-5—No. 11—November 1987.

4. "An Analysis of A Fiber-Optic Magnetometer with Magnetic Feedback"—Koo et al.—Journal of Lightwave Technology—Vol. LT-5—No. 12—December 1987.

The disclosures of these publications are incorporated herein by reference.

SUMMARY OF INVENTION

In view of the foregoing, the main object of this invention is to provide a biomagnetic analytical system which includes a pick-up device employing an array of fiber-optic magnetic (FOM) sensors for measuring and indicating minute magnetic fields emanating from a multitude of sites in the brain or in other tissue regions of interest in a subject being diagnosed.

A significant advantage of a fiber-optic magnetic sensor (FOM) over a SQUID is that the former is a solid-state device that is considerably smaller than the latter and requires no cryogenics, thereby making it possible to distribute a multitude of the sensors (i.e., in excess of forty) around the skull of the patient or about any other tissue region of interest to effect more accurate localization of magnetic activity, as well as a more precise determination of the physiological condition of the region being studied.

More particularly, an object of this invention is to provide a system of the above type for MEG analysis in which the FOM sensors are so distributed in a three-dimensional array as to pick up magnetic fields emanating from a multitude of brain sites simultaneously and to spatially localize the field signals.

Also an object of the invention is to provide a shielded magnetic pick-up device in which the FOM sensors in the array are magnetically shielded from each other to prevent magnetic interaction therebetween, as well as from magnetic fields extraneous to the region of interest, thereby obviating the need for a shielded room to conduct studies on biomagnetic activity.

Yet another object of the invention is to provide a biomagnetic system in which the outputs of the FOM sensors in the array are multiplexed, whereby a common interferometer can be used for the multitude of sensors in the array thereof.

Briefly stated, these objects are attained in a biomagnetic analytical system for sensing and indicating minute magnetic fields emanating from the brain or from any other tissue region of interest in a subject under study. The system includes a magnetic pick-up device constituted by an array of fiber-optic magnetic sensors mounted at positions distributed throughout the inner confines of a magnetic shield configured to conform generally to the head of the subject or whatever other body region is of interest.

Each sensor yields a light beam whose phase or other parameter is modulated in accordance with the magnetic field emanating from the related site in the region. The modulated beam from each sensor is compared in an interferometer with a reference light beam to yield an output signal that is a function of the magnetic field being emitted at the related site. The output signals from the interferometer are processed to provide a display or recording exhibiting the pattern or map of magnetic fields resulting from emanations at the multitude of sites encompassed by the region.

BRIEF DESCRIPTION OF DRAWINGS

For a better understanding of the invention as well as other objects and further features thereof, reference is made to the following detailed description to be read in conjunction with the accompanying drawings, wherein:

FIG. 1 is a perspective view of a magnetic field pick-up device in the form of a helmet which is fitted over the head of a patient and which incorporates an array of FOM sensors for simultaneously detecting magnetic fields emanating from a multitude of sites in the brain;

FIG. 2 shows the helmet partially cut away to expose an inner insulating liner on which the sensors are mounted;

FIG. 3 is a separate view of the inner liner, illustrating the manner in which the FOM sensors are shielded from each other;

FIG. 4 illustrates, in perspective, a cylindrical magnetic pick-up device;

FIG. 5 shows a semi-cylindrical section of the pick-up device;

FIG. 6 shows a flat pick-up magnetic device;

FIG. 7 illustrates a unit for accommodating a patient undergoing a magnetoencepahlographic examination; and FIG. 8 illustrates schematically a biomagnetic analytical system in accordance with the invention operating in conjunction with a pick-up device that is appropriate to the region being studied.

DETAILED DESCRIPTION OF INVENTION

FOM Pick-Up Devices

Referring now to FIGS. 1 to 3, there is shown one preferred embodiment of a pick-up device 10 in accordance with the invention, adapted to detect magnetic fields emanating from a multitude of sites on the brain of a patient for purposes of magnetoencelographic (MEG) examination.

Pick-up device 10 includes a generally spherical helmet 12 formed of ferromagnetic or superconductive shielding material, the helmet being configured to generally conform to the head of a patient 11 so that the brain therein lies within the confines of the helmet, and the weak magnetic fields emanating from the brain are confined within the helmet which acts to exclude extraneous magnetic fields, including those emanating from external electronic equipment associated with the pick-up device.

Helmet 12 is provided with a conforming inner liner 13 formed of electrical insulating material, such as in synthetic plastic material or an epoxy compound having good dielectric properties. Embedded in liner 13 or otherwise mounted thereon is a three-dimensional array of identical FOM sensors 14, each provided with a fiber-optic light conducting line 15 to supply light from a suitable laser beam source to the sensor and to conduct the light modulated by the sensor in response to the magnetic field detected thereby to an external interferometer. Lines 15 are bundled to form a cable 16 running from the pick-up device to external signal processing apparatus.

The FOM sensors 14 in the three-dimensional array are distributed uniformly throughout the inner confines of helmet 12, so that each sensor acts to pick up a unique magnetic field emanating from the head.

As shown in FIG. 3, FOM sensors 14 are internally shielded from each other but not from the magnetic fields emanating from the brain by an open cell ferromagnetic honeycomb 17 so that there is no magnetic interaction between the sensors.

Fiber-optic magnetometers are well known, as evidenced by references (1) to (4), supra. The operation of FOM sensor is based on the transference of strain from the magnetostrictive material in response to a magnetic field to the core of the optical fiber via mechanical bonding, resulting in a phase modification of the propagated light beam. The modulated light from the sensor is subsequently processed in an interferometer which may take the form of a photodetector which compares the phase-modulated light beam with a reference light beam to provide an output signal that is a function of the phase displacement caused by the magnetic field to which the sensor is exposed.

FOM sensors are available in various configurations. In one such configuration, the optical fiber is bonded to a magnetostrictive element to form a waveguide strip that is then coiled into a spool so that the entire sensor is very small. For alternating-current measurements using, for example, metallic glasses as the sensing material, magnetic sensitivities of the order of $10^{-9}$ G/m of fiber core are obtainable.

Design improvements such as magnetic feedback nulling (Reference 4) can lead to improvements in the linear dynamic range, high suppression of magnetic hysteresis associated with the magnetic material, and improved long-term stability. Methods of improving fluctuations of the transmission characteristics of the fiber (induced by the surrounding environment) exist such as use of phase-sensitive transducers combined with a single polarization-maintaining fiber. Thus polarization-rotated reflection can be used to enhance the performance of the system.

Of the many configurations the magnetometer can take, all detect an externally-induced optical phase shift. The sensitivity of the system is proportional to the length of the fiber, until such time as the length approaches the point where other optical properties of the fiber interfere with the propagation of light. The measurement of the linear strain in length of the fiber which is bonded to (or coated by) the magnetostrictive material forms part of one arm of a fiber interferometer. Several types of interferometer designs have been employed, among which are the Fabra Perot, Mach Zender, Michelson and Sagnac types. Well designed interferometers can detect induced optical phase shifts below $10^{31\ 6}$ rad over the frequency range of $10-10^4$ Hz. Thus, very weak magnetic fields per meter of fiber can be detected.

The sensor configuration can be a fiber bonded to a magnetostrictive tube or mandrel, a metal film deposited on the fiber, a metallic glass strip bonded to fibers or a metallic glass cylinder. The magnetic materials which are sensitive in the range of DC to 50 kHz are nickel, iron-nickel alloys, cobalt-nickel, and metallic glasses. Piezoelectric activity in the jacket of the fiber can be achieved by the use of various types of polymer films.

Sensing of small AC magnetic fields at optimal DC bias magnetic fields for various frequencies can occur. The AC measuring technique enables the separation of the magnetic effect (at relatively higher frequencies)

from environmental effects (such as temperature or acoustics at lower frequencies) on the fiber interferometer. Thus, the fiber interferometer can be stabilized without losing sensitivity to magnetic fields.

To extend the AC measuring technique to measure DC bias magnetic fields, one can make use of the effect of DC bias magnetic fields to change the interferometer output due to a fixed AC magnetic field drive at a given frequency. In a sense, this technique utilizes an AC approach to measure DC magnetic fields, thereby overcoming both the environmental perturbation and the 1/f noise problem usually associated with low frequency measurements. It is the nonlinear response of the magnetostrictive material that allows the utilization of an AC technique to measure DC magnetic fields.

In the helmet-type pick-up device shown in FIGS. 1 to 3 which is adapted for MEG studies, each FOM sensor 14 in the three-dimensional array thereof is oriented so that the longitudinal axis of the optical waveguide coil or spool is substantially perpendicular to the surface of the skull of patient 11 wearing the helmet. This orientation makes it possible to dispose a multitude of sensors (forty or more) at positions distributed uniformly about the skull. The density of the coils in the array is limited by factors such as the physical diameter of each spool and induced noise from nearby spools such as eddy currents.

In biomagnetic measurements, sensitivity is limited by fluctuations in the ambient fields and not the intrinsic noise of the sensor. Such ambient fields are produced primarily by the sensor itself, motorized machinery and metallic structural components of buildings which distort the earth's geomagnetic field. The earth's geomagnetic field is uniform and steady. The problem arises when a sensing system vibrates, often in the 1–10 Hz range. Also, the subject may produce noise from normal physiological activity. In MEG, the head proper is the source of a significant amount of noise, produced primarily by the cortex. But because the array of sensors lies within a shield and each sensor occupies a position within a cell in a honeycomb shield, the sensors are isolated from ambient noise and magnetic interaction therebetween is prevented.

Each sensor acts as a gradiometer of predetermined order, any three of which can be used to localize biomagnetic sources at any brain site by the use of the computation techniques described hereinafter.

The pick-up device shown in FIGS. 1 to 3 is adapted to be placed over the head of a patient for MEG analysis. But in practice, the pick-up device can be customized to pick up magnetic field activity arising in other body regions of interest. Thus in measuring magnetic fields generated by the heart, the appropriate pick-up device, as shown in FIGS. 4 and 5, is in a cylindrical form composed of a pair of complementary semi-cylindrical sections 18 and 19 which are joined together by Velcro fasteners 20 or similar means which makes it possible to detach the sections from each other. In practice, for heart analysis, the cylinder is positioned around the thorax.

The cylinder is constituted by an outer shell 21 of shielding material having an inner liner 22 of insulating material in which are embedded a cylindrical array of FOM sensors 23. This cylindrical array of sensors surrounds the thorax, each sensor picking up the magnetic field emanating from a respective site in the heart.

The cylindrical pick-up device can also be configured to go around a limb to measure magnetic fields generated by the muscles therein. For other parts of the body, a flat pick-up device may be appropriate. This flat device, as shown in FIG. 6, is provided with an outer metal plate 24 of shielding material laminated to an inner block 25 of electrical insulating material in which a rectangular array of FOM sensors 26 is embedded.

In practice, the cylindrical pick-up device may be applied to any extremity; and a semi-cylindrical pick-up section can be used separately for measurement purposes. The flat pick-up device is useful for small surface measurements.

In practice, the pick-up device may be contoured to conform to any body region of interest. Thus the pick-up device can be used in a broad range of medical applications by making available to the practitioner a family of pick-up devices, each customized for a particular part of the body. The pick-up device is strapped or otherwise attached to the body part when a biomagnetic study is to be conducted.

For MEG procedures, as shown in FIG. 7, the helmet-type pick-up device 10 may be included as the headpiece of a support unit 27 which also provides a seat, a back rest and a foot platform for the patient whose head is received by the helmet. Housed in the unit is electronic equipment for processing the outputs of the FOM array contained in the helmet.

If one wishes to conduct biomagnetic studies on all portions of the body with a single pick-up device, the pick-up device for this purpose (not shown) may take the form of a sarcophagus-like magnetically shielded enclosure with suitable breathing vents, within which enclosure are disposed arrays of FOM sensors to pick up magnetic fields from different regions of the body. In practice, various standard electronic techniques can be used for noise reduction, either separately or in combination with physical shielding.

The Biomagnetic Analytical System

As shown in FIG. 8, one preferred embodiment of a biomagnetic analytical system in accordance with the invention includes a magnetic field pick-up device 28 in a configuration appropriate to the region under study. Device 28 includes an outer shield 29 within which is an array of FOM sensors 30, each coupled by a fiber-optic line 31 to the input of a multiplexer 32 whose output is applied to an interferometer 33.

Thus instead of having a separate interferometer channel for each FOM sensor which would be very costly, a common interferometer now serves sequentially to compare the modulated light beam derived from each sensor in the array with a reference light beam to produce an output signal. This output signal is a function of the sensed magnetic field emanating from the site related to the sensor.

In practice, multiplex transmission of the signals from the interferometer may be either optical or electrical; that is, by optical waveguides or by conductive wires in the case where the interferometer is of the type which applies the modulated light signal to a photodetector to be compared with the reference light beam.

The output signals from interferometer 33 representing the sensed magnetic fields is applied to a data acquisition stage 34.

The output of interferometer 33 is phase information related to the degree of phase rotation resulting from the detection of the incident vector of the magnetic field transient on the fiber optic sensor. This phase information can evolve over time as the biomagnetic signal progresses, and it is of an analog nature. Therefore, it can be acquired, recorded, and processed in either the analog or digital form. For purposes of the present embodiment, reducing the data to, and processing the data in digital form will be discussed. However, the specific means of data handling is not important to the invention.

Time-varying phase information can be represented in the form of an evolving analog voltage which is proportional to the phase shift by a predetermined relationship. This signal can be converted to digital form through a conventional high speed sample-and-hold and analog-to-digital converter (ADC) means whereby the resulting bandwidth of the recorded signal can be limited to that which is determined by the sampling rate of this analog signal according to the Nyquist sampling theorem.

Since the signal from each sensor on the sensor array is time-multiplexed before entering data acquisition stage 34, a single ADC system is sufficient to digitize the signals from the entire sensor array. However, it should be noted that due to the signal bandwidth requirements and the size of the sensor array, it might be possible that the amount of data generated may result in a data rate which is high enough that the conversion rate of a single ADC might be exceeded and thus, a single ADC channel would not suffice. In this case, the multiplexed signal must then be de-multiplexed, the data from each sensor within the array then being directed to a respective ADC channel, there being one ADC channel per sensor, for example.

In practice, several electronic methods may be used to reduce noise, including the use of comb filters, subtracting a reference channel from a signal channel, adaptive filtering of analog or digital format or balancing of detectors. These can quite effectively reduce the ambient noise, even to the point where physical shielding may not be necessary.

The system lends itself to any number of data acquisition and processing means. For example, since the phase information in a magnetoencephalographic signal can be presented in optical form, the data is particularly suited to processing by optical computer technology.

The output of data acquisition stage 34 is applied to a data processing stage 35. Through the applications of standard spatial localization algorithms, such as are addressed by point source theory, a three-dimensional histogram map can be generated to represent the location and relative magnitude of each magnetic dipole source. The processing of the data will depend upon the configuration of the sensor array, since the proper 3-D mapping of the magnetic dipoles mandates a predetermined geometry of the plane of the array as well as the spacing between each sensor element within the array.

Once the data is acquired in digital form, it can be immediately processed by conventional digital computer means for the purposes of relating the data in various formats including those clinically relevant such as (a) time-varying analog and bandwidth information for each channel, and (b) the spatial localization, through the application of point source theory, of the magnetic dipoles which generated the magnetic field transients that were detected by the sensor array. The data can also be directed to a storage medium for the purpose of recording the digitized biomagnetic data for archiving and later retrieval and processing.

Additionally, other correlative modalities may be employed in conjunction with the biomagnetic data in order to obtain more complete information about a particular body tissue or system. Thus, modalities such as EEG, EKG, MRI and X-ray from a source 36 can be combined with the biomagnetic data in the data processing stage 35 and represented according to the particular need of the practitioner.

The output of data processing stage 35 is applied to a data reduction stage 37. The computational techniques necessary for resolution of the image and decoding it into a meaningful "image" for the clinician to interpret requires Fourier analysis of the affected light similar to the analyses utilized by the magnetic resonance imaging (MRI) technology. The FOM-based system in accordance with the invention allows for the detection of a large number of points simultaneously. This feature is most important, since clinicians have long sought a method of actually visualizing the physiological processes of the intact brain (especially deep brain structures) in various states of sleep and consciousness.

Two major problems encountered by the conventional SQUID-based system for MEG is that the resolution is not very good, and that the number of sensors that can be employed is quite limited, thereby limiting the sites in the brain that can be "scanned" for possible pathologies. These two cumbersome problems are overcome with the FOM-based system, making possible many more clinical applications.

With regard to the actual diagnosis of pathologies, the system is targeted toward the same professionals for whom the conventional SQUID-based system is designed. Primarily. these are radiologists, neurologists and surgeons. For example, the practitioner could "see" a functional image of the brain on a CRT, but the image will be a profile of the electromagnetically "active" portions of the brain, as shown by the magnetic pattern 38 derived from data reduction stage 37. The display plane can represent the location of each magnetic dipole source, and one pixel intensity can represent the magnetic dipole magnitude or phase with respect to a reference signal. What these active areas mean, and how they relate to pathologies is currently an area of intense interest in the basic and clinical neurosciences. Such areas of activity might signify anything from a soft-tissue pathology to abnormal behavioral patterns where no morphological or biochemical anomaly can be detected.

The format of data presentation can take the form of a static or time-varying uni- or multi-dimensional display.

Uni-dimensional display conforms to the current standards of SQUID-based magnetometry and of clinical electrophysiology. In this case, data is represented as linear time-varying representations of single detector elements. Multi-dimensional analysis can provide two- or three-dimensional graphic representations of the data. These multi-dimensional constructs are the result of applying the point source theory algorithms referred to above and can represent the dipole data spatially, or in terms of other dimensionalities, such as k-space in the Fourier domain.

Thus, the three-dimensional histogram map which can be representative of the location and relative magnitude of each magnetic dipole source can be rendered on a standard graphic workstation 39. Application-specific labelling must be applied to convey orientation and scaling of the 3-D data matrix. The display may take the graphical form 40 in which the level of each sensed field derived from the FOMs is represented by a column. Or the levels may be separately indicated on a record chart 41.

Advantages

The main advantages of the system are as follows:

I. Each FOM-based sensor is far smaller than a SQUID-based sensor. Thus, a multitude of FCM sensors can be placed over or around the region of interest by the magnetic pick-up device.

II. A system of gradiometers of predetermined order allows for a more accurate localizatior of biomagnetic activity, and a precise determination of the physiological condition.

III. The system affords more freedom to investigate several areas of the tissue region of interest simultaneously, since it provides a means to spatially localize the field signals.

IV. The biomagnetic analyzing system does not use expensive cryogens. The FOM-based pick-up device entails minimal installation time and service requirements.

V. The FOM sensor is relatively easy and inexpensive to construct, since only "solid-state" materials are required.

VI. The magnetic shielding needed for the FOM-based biomagnetic monitoring is limited to the area surrounding the region of interest, thereby eliminating the need for a specially shielded room.

VII. Even if a shielded room or enclosure is preferred for added noise reduction, the enclosure need not be larger than that required to placed the patient in comfortably.

VIII. Multiplexing the output from the sensing array makes it possible for more sensors to be monitored with fewer "decoding" devices at the "back end."

IX. The FOM-based pick-up device produces optical data that lends itself to optical computing available through the field of "photonics" involving optical processing technologies which can drastically decrease data processing times without compromising resolution.

While there has been shown and described a biomagnetic analytical system using various embodiments of FOM pick-up devices in accordance with the invention, it will be appreciated that many changes and modifications may be made therein, without, however, departing from the essential spirit thereof.

We claim:

1. A biomagnetic analytical system for sensing and indicating minute magnetic fields emanating from the brain or any other tissue region of interest in a subject being diagnosed, said system comprising:
   (a) a magnetic pick-up device having an outer shell contoured to conform generally to the region of interest, said shell being formed of magnetic shielding material to exclude from its inner confines extraneous magnetic fields, whereby the emitted magnetic fields exist within the confines of the shell, and an array of fiber-optic magnetometer sensors which conforms to the contours of the shell, the sensors being mounted within the shell at positions distributed throughout the inner confines thereof, whereby each sensor is related to a site in the region and yields a light beam modulated in accordance with the magnetic field emanating from this site; and
   (b) means including an interferometer to compare the modulated light beam yielded by each sensor in the array with a reference light beam to produce an output signal that is a function of the magnetic field emitted at the related site.

2. A system as set forth in claim 1, wherein said sensors are each disposed within a respective cell of a honeycomb shield supported within the shell to prevent magnetic interaction between the sensors.

3. A system as set forth in claim 1, wherein said sensors in the array are supported on an electrically insulating inner liner conforming to the inner contours of the shell.

4. A system as set forth in claim 1, wherein said shell is configured as a helmet to be worn by the subject for brain magnetic field diagnosis.

5. A system as set forth in claim 1, wherein said shell is configured as a cylinder for heart magnetic field diagnosis.

6. A system as set forth in claim 1, further including means coupled to the output of said interferometer to process the output signals from the interferometer to provide a display exhibiting the pattern of magnetic fields emanating from the sites encompassed by the region.

7. A system as set forth in claim 1, wherein said array has at least forty sensors.

8. A system as set forth in claim 1, wherein the modulated light beams from the sensors are applied sequentially to the interferometer through a multiplexer.

* * * * *